US009693952B2

(12) United States Patent
Potter et al.

(10) Patent No.: US 9,693,952 B2
(45) Date of Patent: Jul. 4, 2017

(54) SOLID PHARMACEUTICAL AND VACCINE DOSE

(71) Applicant: GLIDE PHARMACEUTICAL TECHNOLOGIES LIMITED, Oxfordshire (GB)

(72) Inventors: Charles David Ogilvy Potter, Oxfordshire (GB); Shohre Nabahi, Bampton (GB)

(73) Assignee: GLIDE PHARMACEUTICAL TECHNOLOGIES LIMITED, Oxfordshire (GB)

( * ) Notice: Subject to any disclaimer, the term of this patent is extended or adjusted under 35 U.S.C. 154(b) by 0 days.

(21) Appl. No.: 15/201,791

(22) Filed: Jul. 5, 2016

(65) Prior Publication Data

US 2016/0310413 A1    Oct. 27, 2016

Related U.S. Application Data

(60) Continuation of application No. 14/095,101, filed on Dec. 3, 2013, which is a division of application No. 12/527,980, filed as application No. PCT/GB2008/000589 on Feb. 20, 2008, now abandoned.

(30) Foreign Application Priority Data

Feb. 22, 2007 (GB) .................................. 0703507.4
Nov. 28, 2007 (GB) .................................. 0723310.9

(51) Int. Cl.
*A61K 9/00* (2006.01)
*A61K 9/16* (2006.01)
*A61K 39/05* (2006.01)
*A61K 39/102* (2006.01)
*A61K 31/4045* (2006.01)
*A61K 31/4468* (2006.01)
*A61K 47/10* (2017.01)
*A61K 47/26* (2006.01)
*A61K 47/36* (2006.01)
*A61K 39/00* (2006.01)

(52) U.S. Cl.
CPC .......... *A61K 9/0021* (2013.01); *A61K 9/0024* (2013.01); *A61K 9/1641* (2013.01); *A61K 31/4045* (2013.01); *A61K 31/4468* (2013.01); *A61K 39/05* (2013.01); *A61K 39/102* (2013.01); *A61K 47/10* (2013.01); *A61K 47/26* (2013.01); *A61K 47/36* (2013.01); *A61K 2039/545* (2013.01); *A61K 2039/55505* (2013.01); *A61K 2039/575* (2013.01)

(58) Field of Classification Search
None
See application file for complete search history.

(56) References Cited

U.S. PATENT DOCUMENTS

| 5,542,920 A | 8/1996 | Cherif Cheikh |
| 5,916,588 A | 6/1999 | Popescu et al. |
| 6,565,888 B1* | 5/2003 | Tracy .................. A61K 9/1647 424/130.1 |
| 2003/0054044 A1 | 3/2003 | Potter et al. |
| 2005/0202072 A1 | 9/2005 | Buch-Rasmussen et al. |
| 2006/0171917 A1 | 8/2006 | Campbell |
| 2007/0003576 A1 | 1/2007 | Gambotto et al. |
| 2007/0077253 A1* | 4/2007 | Haynie .................. A61K 39/00 424/184.1 |
| 2010/0119570 A1 | 5/2010 | Potter et al. |
| 2014/0093553 A1 | 4/2014 | Potter et al. |

FOREIGN PATENT DOCUMENTS

| EP | 0 049 068 | 4/1982 |
| EP | 1 250 936 | 10/2002 |
| GB | 2 091 554 | 8/1982 |
| WO | WO 94/22423 | 10/1994 |
| WO | WO 96/08289 | 3/1996 |
| WO | WO 00/62759 | 10/2000 |
| WO | WO 03/023773 | 3/2003 |
| WO | WO 03/051328 | 6/2003 |

OTHER PUBLICATIONS

Bretsch et al, Media release. The American College of Preventive Medicine (ACPM). ACPM recommends research priorities for child and adolescent immunizations. Media Release: Aug. 13, 2003. Available from: URL: http://www.acpm.org, USA, Aug. 13, 2003 retrieved on Oct. 21, 2015.
Notice of Allowance mailed Jul. 11, 2016 in U.S. Appl. No. 14/095,101 (Potter et al., Title: Solid Pharmaceutical and Vaccine Dose), filed Dec. 3, 2013.
Amended claims filed Jun. 6, 2016 in U.S. Appl. No. 14/095,101 (Potter et al., Title: Solid Pharmaceutical and Vaccine Dose), filed Dec. 3, 2013.

* cited by examiner

*Primary Examiner* — Oluwatosin Ogunbiyi
(74) *Attorney, Agent, or Firm* — Nixon & Vanderhye P.C.

(57) ABSTRACT

An elongate body for parenteral injection at low velocity from a device is described. The body has at least one pointed end and comprises at least one active material. In addition, the body has a compressive strength of greater than or equal to 5 Newton and the pointed end has an included angle of between about 10-50°. A solid vaccine formulation for needle-free parenteral delivery, methods for making the body, packaging of the body and use of the body, packaging and suitable delivery device are also described.

35 Claims, 5 Drawing Sheets

Figure 1

SOLID PHARMACEUTICAL AND VACCINE DOSE

Figure 2:
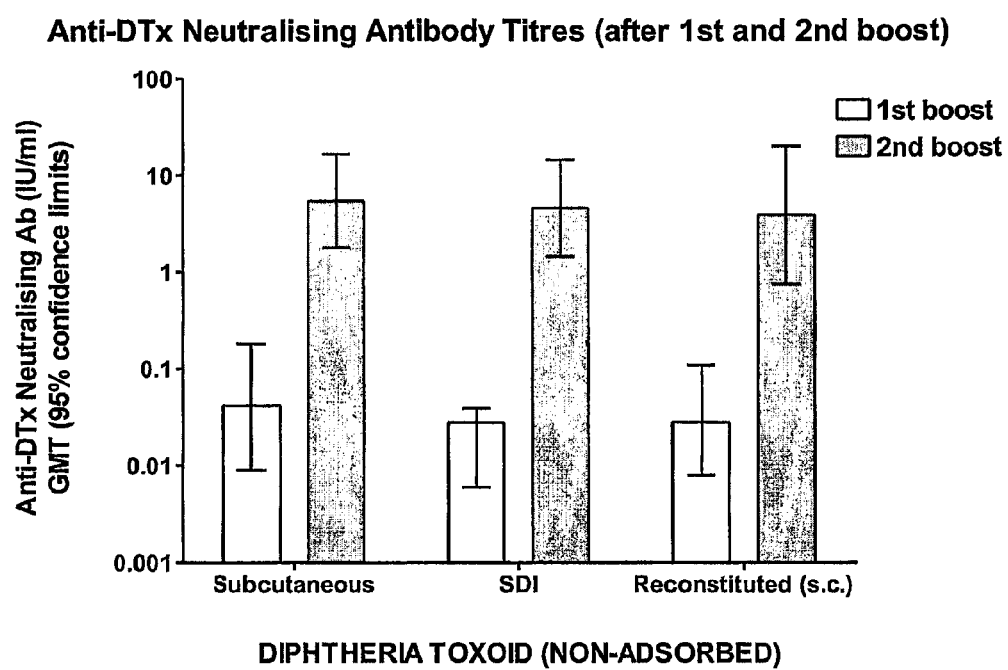

This application is continuation of U.S. application Ser. No. 14/095,101 (pending), filed Dec. 3, 2013 (published as US 2014-0093553 A1), which is a divisional of U.S. application Ser. No. 12/527,980 (abandoned), filed Aug. 20, 2009 (published as US-2010-0119570-A1), which is a U.S. national phase of International Application No. PCT/GB2008/000589, filed 20 Feb. 2008, which designated the U.S. and claims priority to GB 0703507.4, filed 22 Feb. 2007 and GB 0723310.9, filed 28 Nov. 2007, the entire contents of each of which is hereby incorporated by reference.

The present invention relates to an elongate body and solid formulation for parenteral injection at low velocity from a device, which can be used with a needle-free injector. The body has at least one pointed end and comprises at least one active material, which can be a vaccine. In addition, the body has a compressive strength of greater than or equal to 5 Newton and the pointed end has an included angle of between about 10-50°.

A vaccine is an antigenic preparation used to establish immunity to a disease. Vaccines can be prophylactic (e.g. to prevent or ameliorate the effects of a future infection by any natural or "wild" pathogen), or therapeutic (e.g. vaccines against cancer).

There are four types of traditional vaccines. Vaccines containing killed microorganisms are derived from previously virulent micro-organisms that have been killed with chemicals or heat. Examples are vaccines against flu, cholera, bubonic plague, and hepatitis A. Vaccines containing live, attenuated microorganisms are derived from live micro-organisms that have been cultivated under conditions that disable their virulent properties. They typically provoke more durable immunological responses and are the preferred type for healthy adults. Examples include yellow fever, measles, rubella, and mumps. Toxoids are inactivated toxic compounds from micro-organisms in cases where these (rather than the micro-organism itself) cause illness. Examples of toxoid-based vaccines include tetanus and diphtheria. Rather than introducing an inactivated or attenuated micro-organism to an immune system, a fragment of the micro-organism can create an immune response. Characteristic examples include the subunit vaccine against HBV that is composed of only the surface proteins of the virus (produced in yeast) and the virus-like particle (VLP) vaccine against human papillomavirus (HPV) that is composed of the viral major capsid protein.

A number of innovative vaccines are also in development and in use. Certain bacteria have polysaccharide outer coats that are poorly immunogenic. By linking these outer coats to proteins (e.g. toxins), the immune system can be led to recognise the polysaccharide as if it were a protein antigen. This approach is used in the *Haemophilus influenzae* type B vaccine. Alternatively, by combining the physiology of one micro-organism and the DNA of the other, immunity can be created against diseases that have complex infection processes. In recent years a new type of vaccine, created from an infectious agent's DNA, called DNA vaccination, has been developed. This works by insertion (and expression, triggering immune system recognition) into human or animal cells, of viral or bacterial DNA. Some cells of the immune system that recognise the proteins expressed will mount an attack against these proteins and cells expressing them. Because these cells live for a very long time, if the pathogen that normally expresses these proteins is encountered at a later time, they will be attacked instantly by the immune system. One advantage of DNA vaccines is that they are very easy to produce and store.

The prophylactic use of vaccines has been practiced for many decades to protect against a wide range of diseases. Some vaccination campaigns have been so successful that a number of diseases are now rare in many parts of the world. Many new vaccines are in development for either therapeutic and/or prophylactic use.

Most vaccines must be administered via an injection, although a few vaccines have been developed for oral or nasal administration. Injections have traditionally been administered with a needle and syringe with the vaccine in a liquid form. This technique has a number major drawbacks, in particular, needle phobia (reduced compliance), liquid formulation (stability and cold chain storage issues), and needle disposal (potential for cross contamination). Some vaccines are not sufficiently stable in a liquid form, even if they are refrigerated, and these have to be kept as a powder. Prior to injection these powders must be reconstituted, adding further complexity to the process.

Micro-needle patches are in development for vaccinations. These have tiny microneedles which are either coated in antigen or which have tiny holes in them through which the antigen can be pushed. The microneedles are inserted into the outer layers of the skin to benefit from the enhanced immunogenicity in the skin.

Vaccines for nasal administration have also been developed, to benefit from the delivery to nasal mucosa. However, these systems are very expensive to produce. A small number of oral vaccines are commercially available and other routes of administration are in development but these are unlikely to be in routine use for many years, if at all.

There are many different routes for delivering therapeutic compositions. In general, oral administration is the preferred route since many drug substances are readily absorbed in the gastrointestinal tract. It is also a form of administration that is well accepted by patients and usually results in good patient compliance. However, not all drug substances can be formulated for oral delivery and such an administrative route does not always provide the optimal bioavailability of a drug.

One route of administration that circumvents the gastrointestinal tract is referred to as parenteral administration and it is commonly the route of choice for drugs that are degraded or are erratically or unreliably absorbed when administered orally.

The skin is one of the more efficient routes for parenteral delivery of a therapeutic compound and such administration is most commonly undertaken using a needle and syringe as a delivery system, with the therapeutic compound in a liquid form. The needle and syringe delivery system has a number of drawbacks, including the pain and fear associated with needles, the requirement for a liquid formulation and the sharp hazard created by using and disposing of needles.

Needleless drag delivery systems can be used for injecting liquids through the skin. Such a delivery method is typically achieved by creating a very fine, high velocity liquid jet that creates its own hole through the skin. There are however a number of problems with such a method, including splash back.

With both forms of liquid delivery, relatively large volumes of liquid are injected which, because the liquid is incompressible, have to tear the tissue apart in order to be accommodated. In addition, not all therapeutic compounds have a good solubility in water, resulting in the requirement to add potentially toxic additives or surfactants to the solution. In addition, an aqueous solution of any given therapeutic is typically chemically less stable than a dry formulation of the same compound. An aqueous solution is prone to microbial contamination and needs to be sterilized using heat, radiation, filtration or chemical means. Furthermore, the shelf life of an aqueous formulation must usually be enhanced either by the addition of preservatives, stabilizers, anti-oxidants and the like or by special storage conditions at low temperatures to avoid chemical or microbial breakdown of the active ingredients.

Drug injection through the skin does not have to be achieved with the drug in a standard liquid form. Solid form drugs have been successfully administered with the PowderJect system, which uses a compressed gas source to accelerate powdered drugs to a velocity at which the outer layers of the skin can be penetrated. Such a system typically uses powdered drug particles having a diameter of less than 100 microns and requires a velocity of several hundred meters per second to penetrate human tissue. However, the system has its own inherent problems, such as controlled delivery and precise penetration depth. In parenteral injection, it is important to deliver the therapeutic compound to the correct tissue since drugs that do not penetrate the cutis are not taken up by the body, some drugs must reach the muscular tissue or be taken into the blood stream via the subcutis within a predetermined time frame. Energising means used to inject powder particles may include compressed gas and explosives, such as propane, gasoline or gunpowder. Such explosive means provide the administration apparatus with their own inherent potential danger.

It has also been shown that solid rods or splinters of a therapeutic compound can be pushed, at a relatively low velocity, into the skin without the requirement for a needle, although these are more traditionally delivered as implants.

EP 0139286 (Sumitomo Chemical Co Limited) discloses sustained-release preparations in the form of needle- or bar-like shapes which comprise an active ingredient and a pharmaceutically acceptable biodegradable carrier. The sustained release preparation can be administered to the body by injection by pushing it through a hollow needle or by implantation.

U.S. Pat. Nos. 5,542,920, 6,117,443 and 6,120,786 (Cherif Cheikh) disclose needleless parenteral introduction devices and medicaments in the form of a solid needle having a pointed end and sufficient structural integrity to penetrate the skin. The needles are less than 2 mm, preferably 0.2 to 0.8 mm, in diameter and 10 to 30 mm in length.

U.S. Pat. No. 6,102,896 (Roser) is primarily directed to a disposable injector device for injecting controlled release water soluble glass needles. However, it also recognises that these glass needles, which are about 1 mm in diameter by 10 mm in length and contain a medicament, may also be used as pioneer projectiles to produce a low resistance pathway through the tissue along which a liquid suspension (exemplified as a drug in a suspension of PFC fluid) can flow. This document appears the first and only document to recognise that a dissolvable pioneer projectile may be used to enable the introduction of a medicament. However, it fails to recognise that it may be used as a general technique for introducing medicaments in other forms.

WO 03/23773 (Caretek Medical Limited) relates to a method of delivering a solid therapeutic formulation in which a glassy projectile is propelled at low velocity from a device. The projectile creates a passage in the skin that accommodates a therapeutic composition that follows behind, independently of the projectile.

WO 94/22423 (Bukh Meditec A/S) discloses a solid pharmaceutical composition in the form of a needle-shaped body that must have a shape and strength to enable it to penetrate unbroken skin causing as little tissue damage as possible. To achieve this, the body is an elongated shape with a pointed end that is created by a diagonal cut. The strength is provided by the composition which includes gelatin as a base substance and crystalline or caramelised carbohydrate. Because the body is essentially pushed into the skin from a static start without prior propulsion, the body must have a minimum compressive strength of 15,000 lbs/in$^2$ (approximately 100N/mm$^2$). For a rod having a typical diameter of 0.85 mm, this would result in a crash strength of approx 56 Newton.

WO 94/22423 also discloses a process for preparing the formulation comprising i) mixing a polymer and optionally a filler with an active drug substance, ii) extruding the mixture containing the active drug through a die to form an elongate body, iii) drying the body, and iv) cutting the body to form a pointed end.

WO 00/62759 (Novo Nordisk) describes a solid pharmaceutical composition for parenteral injection comprising at least one therapeutic agent and a carbohydrate binder in an amount of at least 0.5% by weight, in which the carbohydrate binder forms an amorphous matrix. The addition of a non-crystallisation agent is optional. The applicants of WO 00/62759 have found that the use of an amorphous matrix allows the composition to have a lower compressive strength, typically at least 5 Newton and preferably 10 to 40 Newton. However, standard extrusion of the composition tends to incorporate air into the composition resulting in a composition that is not sufficiently strong to penetrate tissue and must be injected by a hypodermic needle, a trocar or similar means. Therefore, strength is imparted to the composition by injection moulding.

The Applicant has identified that there is a need for an improved solid composition for needleless parenteral delivery. In particular, the Applicant has recognised that it is the shape of the composition, especially the geometry of a pointed end, that has a bearing on the force required to enable the composition to penetrate the skin causing minimal pain and damage. The Applicant has also found that a combination of formulation strength and the velocity of the formulation as the composition strikes the skin provides the optimal design for effective penetration. Indeed, providing the composition with some velocity before it strikes the skin allows the composition to have a lower inherent strength. This is in contrast to WO 94/22423 which requires a very high compressive strength (approximately 56 Newton) because little or no velocity is imparted to the composition before it strikes the skin.

Stability of vaccines is one of the biggest issues within the vaccine industry. Large quantities of vaccines are wasted every year due to breakdowns in the cold chain. These issues are particularly acute in developing countries. Thus, the development of vaccines that do not require refrigeration would be a huge boost to the vaccine industry. Thus, the development of vaccines that do not require refrigeration would be a huge boost to the vaccine industry. In addition, many vaccines are unstable and so they are stored in a solid form, typically as a lyophilised powder, which is more stable than a liquid. However, even the solid forms currently available require refrigeration. Currently, vaccines in solid formulations need to be reconstituted prior to injection with a needle and syringe. If the vaccine can be manufactured and stored in a solid dosage form and also administered in this same form then it has the benefits of a more stable formulation without the complications of the reconstitution steps. In addition to the added complications of reconstitution there are the added costs of requiring not just the vaccine but also a separate vial of diluent such as water.

Also, many vaccines do not build up the required immune response after a single administration and a prime administration followed by either one or two 'boost' administrations maybe required to achieve sufficient immunisation. Different antigens have different treatment regimes but the first boost injection is typically administered two to four weeks after the prime and a second boost may be given a further one to six months later. Some vaccines (e.g. for influenza) do not provide lasting protection and so a patient may need to be vaccinated every year. In addition, some vaccines (e.g. for influenza) need to be changed regularly (annually for flu) to ensure that protection is being given against appropriate strains.

With some antigens, the immune response can also be enhanced by adding adjuvants to the formulations. The most common adjuvant is alum (aluminium hydroxide) which is insoluble, although other adjuvants are in development or are already on the market.

It has been demonstrated that the skin is very immunogenic and so, if an intradermal injection can be made, it should result in an enhanced immune response. This offers the potential to use lower doses of antigen to achieve the required immune response. Making a true intradermal injection with a needle and syringe is very difficult and therefore injections are normally given into either the muscle or subcutaneous tissue.

Liquid jet injectors have been developed for mass vaccination campaigns. These technologies still have all the issues associated with liquid formulations and tend to require expensive or complicated power sources. Confidence was lost in this type of system in the past when cross-contamination of diseases was seen in patients due to the vaccination procedure.

The PowderJect technology (now owned by Pfizer) fires powders into the skin which either contain the antigen or which have the antigen coated onto them. The system has been most successful for the delivery of DNA vaccines which are coated onto gold carrier particles. It is believed that the gold particles are small enough to be delivered into the cells of the dermis and it is the intracellular administration that provides the enhanced immunogenicity. However, the system has its own inherent problems, such as controlled delivery and precise penetration depth in different skin types and locations on the body. Energising means used to inject powder particles include compressed gas and explosives, such as helium, propane, gasoline or gunpowder. Such explosive means provide the administration apparatus with their own inherent potential danger. These devices are also complicated and therefore expensive.

The vaccine industry can be split into at least three distinct areas:

Industrialised countries

Developing countries

Biodefence

Each of these three areas has particular needs and priorities as shown in Table 1. The table illustrates the relative importance of different features in the three areas of the vaccine industry. The higher the number, the more important the feature is for that territory.

TABLE 1

Data from Gideon Kersten, Needle-free & Autoinjectors, Management Forum, 22-23 Mar. 2007, London

| Key Features | Developing countries | Industrialised countries | Emergency use (biodefence, pandemic) |
|---|---|---|---|
| Cheap | 5 | 2 | 3 |
| Stable | 4 | 2 | 4 |
| Easy to use | 4 | 1 | 4 |
| "Pain-free"/Needle phobia | 1 | 5 | 1 |
| No adverse effects | 1 | 4 | 1 |
| No cross-contamination | 5 | 4 | 4 |
| Quick to distribute | 2 | 3 | 5 |

Industrialised Countries: Childhood vaccination is the most common type of vaccination in the industrialised world but there is also a big market for travel vaccines. The main issue for vaccinations in industrialised countries is compliance. Patients must believe that the vaccinations are safe and, if they can be administered in a more 'patient-friendly' manner, more people will be vaccinated. In 1998 there were reports in the UK that the combined measles, mumps and rubella vaccinations in babies might be causing autism in some of the children. These reports led to many children not being vaccinated which in turn led to increased outbreaks of measles in the UK. Many new vaccines are in development and these may initially only be marketed in industrialised countries due to cost constraints. These include vaccines against infections such as human papillomavirus (HPV).

Developing Countries: The main issues for vaccination programmes in developing countries are 1) to avoid needles, which are routinely reused and therefore cause the spread of blood-borne diseases such as hepatitis B and HIV, and 2) to have more stable vaccines that do not rely on refrigeration. Maintaining cold chain storage in industrialised countries is challenging enough without having to keep materials cold in parts of the world where ambient temperatures can be high and that often do not have reliable electricity supplies. Reports state that up to 50% of vaccines have to be thrown away due to breakdown in cold chain storage. In addition to the two main criteria set out above, vaccination programmes in developing countries are often funded by charities and so only low cost technologies can be employed in order to vaccinate as many people as possible.

Emergency Use: Following the terrorist attacks in America in 2001, the US Government started to stockpile vaccines to protect against other potential attacks. This includes vaccines such as anthrax and small pox. In addition to the terrorist threat, there is also the threat of pandemic outbreak of diseases such as influenza. At present, the stockpiles of anthrax and small pox vaccines have to be replaced every two to three years due to the limited shelf life of the material, even when it is refrigerated. Thus, the ideal vaccine for stockpiling would be stable for many years at room temperature and would not require trained healthcare professionals to make the injections in the case of an emergency. An ideal technology for delivering stockpiled vaccines would be easy to distribute and easy to use in emergency situations, preferably by non-medical or healthcare personnel.

It is against this background that the Applicant has investigated alternative solutions to currently available technologies. In addition, current technologies typically do not take into consideration the different requirements demanded by the three main areas of the vaccine market. Thus, the Applicant has sought to provide a vaccine formulation and delivery system that overcomes substantially all the problems of existing technologies while providing a solution that is suitable for use in the three main commercial areas.

Accordingly, in its broadest aspect, the invention resides in an elongate body for parenteral injection at low velocity from a device, the body having at least one pointed end and comprising at least one active material, characterised in that the body has a compressive strength of greater than or equal to 5 Newton and the pointed end has an included angle of between about 10-50°. The pointed end may have an included angle of between about 10-40°.

In another aspect the invention resides in a solid vaccine formulation for needle-free parenteral delivery, the formulation comprising one or more antigenic or immunogenic agents. Expressed in another way, the solid formulation is an elongate body, which may be for parenteral injection at low velocity from a device. The active may be inter alia a vaccine. Where the solid formulation comprises a vaccine, the terms "elongate body" and "solid formulation" are used interchangeably.

An antigenic or immunogenic agent is an agent that is capable of inducing an immune response within an animal. An alternative term that is used for such an agent is "antigen" and the two terms will be used interchangeably throughout this specification.

The term "solid" is used in the context of a state in which the matter is firm and stable in shape so that the matter retains its own shape. In particular, the solid formulation has the shape of a solid rod, splinter, bar or needle.

In a preferred embodiment, the solid formulation has at least one pointed end and a compressive strength of greater than or equal to 5 Newton. The pointed end may have an included angle of between about 10-50°. A suitable formulation is described in GB Application No. 0703507.4 (Glide Pharmaceutical Technologies Limited), the contents of which are incorporated herein by reference.

Ideally the elongate body has a shape and inherent strength to enable it to penetrate unbroken skin.

The term compressive strength refers to the strength of the body when compressed longitudinally, from end to end, rather than circumferentially. The Applicant has found that the body must have a strength sufficient for penetration of the skin, such strength typically needing to be greater than or equal to 5 Newton. However, a compressive strength of between 5 and 500 Newton is suitable for achieving penetration of the body with a preferred strength being between 5 and 50 Newton. A yet further preferred strength is between 5 and 20 Newton and more preferably approximately 10 Newton. Alternatively, a compressive strength of between 20 and 50 Newton is preferred with a more preferred strength being approximately 30 Newton.

In another embodiment, the formulation comprises a pioneer projectile in combination with a solid formulation comprising one or more antigens. In this embodiment, the pioneer projectile creates a passage in the skin that accommodates the solid formulation that follows behind, independently of the pioneer projectile. Such an arrangement is described in WO 03/023773 (Glide Pharmaceutical Technologies Limited), the contents of which are incorporated herein by reference.

The body or the solid formulation of the invention is provided with inertia, by pushing, so that it strikes the skin at a low velocity. This inertia enables the provision of a material with a lower compressive strength and provides improved delivery of the body to the desired parenteral location. A velocity of between 0.5 and 50 m/s is preferred, more preferably between 0.5 and 20 m/s, optimally between 0.5 and 10 m/s.

The body will typically have one pointed end with the other end not being pointed. For example, a body may have one flat end and one pointed end, where the pointed end assists the penetration of the target tissue. In an alternative embodiment, the body may have a point on both ends. The Applicant has found that such an embodiment will make the cutting process easier and also facilitates the packaging of the body since specific orientation in the packaging will not be required.

The Applicant has found that the geometry of the pointed end has a bearing on the force required for penetration of the body: the more acute the angle of the end, the lower the force required to push the body into the target tissue. However, if the angle is too acute then it is difficult to manufacture a good pointed end repeatedly. Therefore a preferred included angle of the pointed end is 20-30° and an angle of about 23° has been found to be optimal. The included angle is the angle included by opposing convergent faces of the pointed end, e.g. across the diameter of a cone, or opposing convergent faces of an end with square cross-section or a wedge. Where the end has more than a pair of different opposing faces, e.g. with an elliptical cross-section, or where it tapers with a rectangular cross-section, it is the smallest angle included by two opposing faces. The pointed end may comprise a central 'chisel' tip. The chisel tip may have an included angle of between about 10-50° or 10-40°. In one embodiment, the preferred angle for an oblique cut of the end is about 23 degrees; the end would therefore have an included angle of 46 degrees according to our definition.

The pointed end has a tip that may be flat, conical, part spheroidal, sphenoidal, or fractured. While a tip ending in a sharp point is ideal, in some instances some shaping or blunting of the tip is desired or inevitable as part of the manufacturing process.

Depending on the chemical structure of the active material and the method used to make the body, the body may be at least partly crystalline or at least partly amorphous or glassy.

The active material in the body may selected from the group comprising peptides, proteins, DNA, RNA small molecules, labelled molecules, dyes, antigens, vaccines and whole cell vaccines. Small molecules may be naturally occurring or synthetic and may be organic or inorganic. It will be understood that the labelled molecules may be labelled with any suitable label, including a radioactive or chemical label. Such labelled molecules, as well as dyes, may be used for diagnostic purposes.

In a preferred embodiment, the active material is a pharmaceutically active compound and may be any sort of drug or vaccine, or may be a combination of one or more drugs or vaccines. In the case of some pharmaceutical active materials, such as vaccines, an antigen or antigens may be combined with, or adsorbed to, an adjuvant.

In particular, the pharmaceutically active compound may be used in the treatment of diseases in the fields of endocrinology, oncology, cardiology, infections, dermatology, obstetrics, gynaecology, respiratory, immunology, treatment of hormonal deficiencies, CNS disease, emergency medicines, vaccinations, pain control or diabetes. Such treatment includes prophylaxis and preventative treatment.

The or each antigen may be adsorbed onto the surface of the body, or contained within or as part of the body.

The solid formulation may further comprise one or more adjuvants. In this embodiment, the or each antigen may be combined with, or adsorbed to, an adjuvant. Suitable adjuvants include aluminium hydroxide and aluminium phosphate. Other adjuvants that have been incorporated in products or are in development include squalene, MF59 (proprietary to Novartis), polymer microspheres and oils.

The solid formulation of the invention may be used to inject one or more doses simultaneously in a solid dosage form. Alternatively, the invention allows for the injection of one or more formulations simultaneously. This provides the opportunity for simultaneous administration of a quick dissolving formulation and a slower dissolving or pulsed formulation. In this way, both a prime and boost administration may be given at the same time. The formulations may include an immediate release formulation and/or a controlled release formulation. The formulations may include a continuous release formulation and/or a pulsed release formulation.

Having the vaccine in a solid dosage form with enhanced stability is important if the antigen is to remain viable in the tissue for a number of days or weeks. The ability to immunise patients fully with one injection will not only save time and money by only treating the patient once, but it will also ensure that the patient is fully immunised.

Adjuvants are thought to cause a local 'irritation' in the skin, thereby causing an enhanced immune response. A solid dosage readily causes local irritation in the skin and this effect could be used in addition to the inclusion of any adjuvants that form part of the initial dosage form. Expressed in another way, a sugar based formulation may have an initial adjuvant effect. Rapid dissolving of the sugar leaves other adjuvant particles in the tissue creating a longer lasting and/or secondary irritation. Thus, the solid dosage may elicit a sufficient adjuvant effect to avoid the need for adjuvant particles to be included in the formulation. Alternatively, the solid dosage may elicit a sufficient adjuvant effect so that the dose of adjuvant particles added to the formulation may be reduced. If reduced levels of adjuvant particles are used within the formulation, costs may be saved on the adjuvant and, more importantly, such a formulation places less foreign material in the human, animal or bird that is injected. This is important because adjuvants like aluminium hydroxide do not dissolve in tissue.

A solid dosage form also provides the option of a controlled release formulation. In this way, the immunogenicity of the vaccination may be increased, either by slow continuous release of antigen over time and/or pulsed release of some of the antigen at a predetermined time after the injection. The pulsed release may be achieved automatically by the formulation in the tissue e.g. a slow dissolving coating around a quick dissolving, antigen containing core, so that the antigen is released as a bolus when the outer coating dissolves. Alternatively, pulsed release of the antigen may be triggered by an external stimulus at the time the antigen is to be released.

Alternatively, the solid formulation may dissolve rapidly, providing a concentrated volume of antigen. This high concentration may have an effect on the immunogenicity of the vaccination.

Producing the vaccines in a solid dosage form means that a number of antigens may be formulated together. Multivalent vaccines are already produced but they require significant trials to ensure the individual antigens do not react with each other when in contact in solution. This is overcome with solid dose formulations as antigens are far less likely to react with each other when in a solid state.

A further advantage of a solid formulation is that the optimum immune response may not be found in the standard areas of tissue that are targeted by a needle and syringe injection. Thus, a solid formulation allows administration of an antigen to tissues and areas that provide a higher and more efficient immune response, such as the skin. Thus, in a preferred embodiment, the formulation is suitable for dermal, intradermal, transdermal, subcutaneous or intramuscular administration.

A yet further advantage of a solid formulation is that a lower dose of antigen may be required to achieve a suitable immune response when compared to a needle and syringe formulation. Expressed in another way, the formulation may produce an enhanced immune response. In other words, an increase in the efficiency of vaccination seen with a solid formulation when compared to a liquid formulation administered via needle and syringe. Alternatively or in addition, the dermal, intradermal, transdermal, subcutaneous or intramuscular administration of the formulation may produce an enhanced immune response. This means that either a higher antibody titre could be achieved for the same dose of antigen or alternatively a lower dose of antigen could be used. In this way, a solid formulation provides an opportunity for dose sparing which, in turn, has an impact on the cost of the vaccine material. This also means that more doses may be obtained from a batch of vaccine material. This is particularly important in scenarios such as a pandemic influenza outbreak where demand for a vaccine will far outstrip the available supply.

Even a ten percent reduction of antigen in each injection would provide cost savings but greater efficacy with a solid formulation may lead to only 75%, 50% or 25% of the antigen required compared to a standard liquid, injection with a needle and syringe. However, antigen doses do not typically show a linear dose response in humans and other animals. Therefore, if a formulation or mode of delivery results in an enhanced immune response, when compared to a needle and syringe injection, then only one tenth, or one hundredth or even one thousandth of the dose of antigen typically required for needle and syringe administration may be required to produce the same or an enhanced immune response.

If the antigen dose can be reduced then the dose of adjuvant, if required, may also be reduced to 75%, 50% or 25% of the adjuvant required compared to a standard liquid injection with a needle and syringe. However, if the adjuvant produces a non-linear dose response then a solid dose formulation might only require one tenth, or one hundredth or even one thousandth of the dose of adjuvant to give the same immune response as a needle and syringe.

It will be appreciated that the antigen may be in any suitable form, such as killed, attenuated or combined microorganisms, inactivated toxic compounds, whole or fragments of proteins or polysaccharides, DNA or RNA. The antigen may also be a virosome, a virus-like particle (VLP), complexed or uncomplexed DNA, adeno-associated virus, an alphavirus vector, an adenovirus vector or a poxvirus vector.

The vaccine may be used in the treatment of diseases in the particular fields of oncology, infections, immunology, emergency medicines and vaccinations. Such treatment includes prophylaxis and preventative treatment.

While the quantity of active material or antigen will be determined by the dose required, the active material may be present in an amount of between 0.1% and 99.9% by weight of the body, preferably between 0.1 and 60% by weight and most preferably in an amount of between 0.1 and 35% by weight. If an adjuvant is desired or required in order to improve the efficacy of the vaccine then this may be present in an amount between 0.5% and 99.9% by weight of the body, preferably between 0.5% and 60% by weight and most preferably in an amount between 0.5% and 35% by weight.

The active material may include, or may be included within, an immediate release formulation and/or a controlled release formulation. The active material may include, or may be included within, a continuous release formulation and/or a pulsed release formulation.

In another embodiment, the body further comprises one or more excipients. The excipients are typically required to bulk up the active material, as well as act as a binder to provide a robust dosage suitable for administration. In some cases, the active material may be able to act as the binder and bulking agent, meaning that the body may comprise 100% active material. In some cases, the antigen may be able to act as the binder and bulking agent, meaning that the body may comprise 100% antigen. Where low doses of active material are required, higher proportions of excipients may be used. Ideally, any excipients are GRAS (Generally Regarded As Safe) registered for pharmaceutical use, especially parenteral administration.

A variety of excipients may be used but different excipients have different physical properties and act as binders in different ways. Excipients that are typically used in tablet formulations are often the best binding agents although, if possible, excipients are selected that are already used in parenteral pharmaceutical products. Excipients may be selected to give an immediate release of the active to the systemic circulation or may be selected to provide a sustained or controlled release. If immediate release is required, a highly water soluble excipient or excipients may be used e.g. sugars, polyvinyl pyrrolidone (PVP), polyethylene glycol (PEG). In contrast, if sustained or controlled release of the active material is desired then materials such as biodegradable polymers may be used as the excipients. The phrase "controlled release" refers to formulations where release of the active material includes slow or pulsed release, as well as mixtures of slow and fast release. Such formulations may be for prophylactic or preventative use, as well as therapeutic use.

Disintegrants may also be added, if desired, to assist in the disintegration of the active material. For example, water soluble disintegrants such as celluloses, including sodium carboxy methyl cellulose or PVP or cross-povidone (CPVP), may be used.

As well as providing the physical strength for the formulation, the excipients may also need to provide any chemical stability required by the active material or antigen. Such excipients may enable the final dosages to be stored at room temperature or higher temperatures rather than requiring cold chain storage. These excipients may also provide an increased shelf life and/or protect the active material or antigen through processes, such as ionizing radiation or other forms of sterilization, to ensure that the final dosage is sterile. Examples of stabilising agents include trahalose, histadine, citrates, lactates, amino acids, polyethers and disodium edetate. Drugs and vaccines are typically more stable when stored in a solid dosage form and many current drugs and vaccines are stored as lyophilised powders and reconstituted prior to injection with a needle and syringe. While the antigenic or immunogenic agents may need to be lyophilised before being formulated into a solid formulation, it is the solid formulation that is then administered. No reconstitution is required and the solid formulation imparts a longer shelf-life to the vaccine. The further consideration with lyophilised powders and stability is that a powder has a relatively large surface area. In contrast, the solid formulation of the present invention presents a lower surface area to the atmosphere compared to a powder and so should show improved stability and shelf-life.

Accordingly, the excipients may be selected from the group comprising bulking agents, anti-oxidants such as Vitamin C and metabisulphites, disintegrants, binders, biodegradable polymers, salts and buffers, wetting agents such as poloxamers and polyvinyl alcohol (PVA), adjuvants and stabilising agents.

Typical materials that may be used as excipients include sugars and carbohydrates such as mannitol, lactose, sorbitol, sucrose, fructose, trahalose, rafinose, maltose, glucose, dextrose, dextrans, cyclodextrins, maltodextrins and sodium alginate. Some of these materials may act as binders and/or bulking agents and/or stabilisers depending on the active material. Sugar based formulations typically produce very fast dissolving formulations. Sorbitol is a preferred excipient as it acts as both a binder and a filler/bulking agent and is approved for parenteral administration. Alternative bulking agents may be alkali metal salts, including sodium and magnesium, lactate, citrate, tartrate and gluconate. An alternative binder may be PVP. Sodium alginate has also been used as an excipient to produce robust formulations. The excipient may therefore be sodium alginate.

Stabilizers may be added to increase the shelf life of the product and avoid refrigeration. Also, stabilizers may be added to protect the drug/vaccine from ionizing radiation during sterilization. The body may comprise a stabilising excipient which performs each of these functions, or the body may comprise two or more stabilising excipients, each performing one of these functions.

Suitable salts and buffers include citric acid and sodium citrate, tartaric acid and sodium tartrate, lactic acid and sodium lactate, and maleic acid and sodium maleate.

Other materials that may be used include polyethers, such as polyethylene glycol; polyethers are particularly suitable for quick dissolving formulations. It will be appreciated that polyethers should have a molecular weight above 1000 kDa because, below this molecular weight, the compounds are liquid at room temperature.

If a slower release of the active material to the systemic circulation is required, biodegradable polymer materials may be incorporated. The polymer, such as polylactide-co-glycolide (PLG), poly (lactic-co-glycolic) acid (PLGA), polycaprolactone, polyanhydride and polyorthoesters, may be incorporated as microspheres in a fast dissolving matrix. Alternatively, the polymer may be used as the main bulking agent or binder in the formulation.

It may also be desired to coat a fast dissolving formulation with a slower dissolving material so that the active material within the fast dissolving formulation is released to the systemic circulation hours, days, weeks or months after the administration of the body of the invention to the target tissue.

Preferably, the active material is homogeneously dispersed throughout the body. However, the body may have an inert pointed end or tip with the active material being found in the elongate part of the body. In such an embodiment, the active material may separated from the non-active material in the body by any suitable means.

Alternatively, the antigen may be sprayed onto the outside of the body which therefore acts as a carrier. Preferably, the antigen is homogeneously dispersed throughout the body. However, the body may have an inert pointed end or tip with the antigen being found in the elongate part of the body. In such an embodiment, the antigen may be separated from the non-active material in the body by any suitable means.

Advantageously, the elongate body has a diameter of between about 0.5 mm and 3 mm, although an ideal diameter is between about 0.6 mm and 1.5 mm. The body may have a length of a few millimeters up to about 15 mm, although a length of 2-8 mm is preferred.

It will be appreciated that the body may be of any suitable cross-sectional shape, including ovoid, triangular, circular, obround (a closed figure having two parallel sides and two semi-circular ends), rectangular and polygonal.

In another aspect, the invention resides in a method for making the elongate body of the invention. The method comprises:
i) mixing the at least one active material and any excipients as dry material with a fluid to produce a paste;
ii) forming the paste;
iii) cutting the paste to a shape having at least one pointed end with an included angle of between about 10-50°, the method further comprising drying the paste either before or after the cutting step.

In particular, the method comprises i) mixing the at least one active material and any excipients as dry material with a fluid to produce a paste; ii) forming the paste; iii) drying the paste; and iv) cutting the paste to a shape having at least one pointed end with an included angle of between about 10-50°.

The method may comprise i) mixing the at least one active material and any excipients as dry material with a fluid to produce a paste; ii) forming the paste; iii) cutting the paste to a shape having at least one pointed end with an included angle of between about 10-50°; and iv) drying the paste.

The included angle may be between about 10-40°.

In one embodiment, any excipients may be mixed into a dry homogenous mix before being added to the active material and fluid. Alternatively, some or all of the active material and some or all of one or more excipients may be added to the fluid before mixing with the remaining dry material. One advantage of adding the active material to the fluid, is that it is possible to achieve very good mixing of the active material throughout the formulation. In yet another alternative, some or all of one or more excipients may be added to the fluid before being mixed with the active material and any remaining dry material.

In a further embodiment, a dry mix of the active material and any excipients may be prepared before addition to the fluid if the active material cannot be dissolved or incorporated in a small enough quantity of fluid. In this embodiment, the active material is ideally mixed with an approximately equal quantity of the excipients and mixed thoroughly before adding another equal quantity of excipients and mixing until all the excipients are used. The excipients are preferably added in small quantities to ensure good mixing. Once a homogenous mixture has been created, the fluid is preferably added to the dry material and the resultant mixture formed.

Another advantage of this process is that the method can be undertaken at or below room temperature. Elevated temperatures, even for short periods of time, can cause degradation of proteins and peptides. Thus, a temperature of above 4° C., preferably ambient temperature is advantageous, with an optimal temperature being between 18° C. and 22° C.

The Applicant has found that the addition of a fluid to the dry materials lubricates the mixture and makes formation easier and more reliable and significantly increases output from the process. The fluid is, in essence, a granulation fluid as it granulates the dry materials. While the preferred granulation fluid is water, any other fluid can be used that does not damage the formulation and will allow the formulations to dry (i.e. not oils). The granulation fluid is preferably a slimy and might be an alcohol, solvent or other buffered solution. In this context, a buffered solution is a solution that contains salts or chemicals. Such salts or chemicals typically act to stabilise the active material.

An important aspect of the process is the quantity of granulation fluid that is added to the dry material to ensure that the formed material is neither too dry as a 'shark skin' rather than smooth appearance) or too wet (cannot hold its shape under its own weight). Thus, the fluid is preferably added to the dry material in an amount of less than or equal to 10-30% volume by weight, ideally approximately 15% volume by weight of the dry material.

Particle size can make a difference to strength of the formulations. The at least one active material and/or and any excipients may be in the form of particles. The particles may be of a standard or uniform size, for example a standard or uniform diameter, or longest dimension. Such standardised particles may provide better strength for the elongate body of the invention.

In another embodiment, the method additionally includes grinding the dry material.

A particle size of from 0.1-1000 micrometers in diameter is advantageous, while a particle size is less than 500 micrometers in diameter is preferred and a particle size is less than 300 micrometers in diameter is still further preferred.

The method may therefore include either starting with active(s)/excipient(s) in particulate form, or grinding same into particles.

In some cases, it might be desirable to use higher temperatures for the formation of the body. Therefore, the method may further include softening or melting the paste either before or after the paste is formed. The temperature of the paste is raised such that at least one of the excipients or the active material softens or melts and, as it cools, it hardens and acts as a binder. A drawback of raising the temperature of the paste is that the active material is necessarily heated which may cause some degradation of the active material. In addition, the materials either need to be mixed thoroughly in the solid form prior to the partial melting, which means that a homogenous mixture is more difficult to achieve, or the materials are mixed in a molten or partially melted form requiring the materials to be kept at a higher temperature for a longer period of time.

However, the Applicant has found that, in some instances, raising the temperature to soften or melt the mixture is desired and even preferred. The softened or melted material is in a pasty condition for further forming. Accordingly, in a yet further embodiment, the invention also resides in a method for making the elongate body of the invention, the method comprising i) mixing the at least one active material and any excipients in a dry form to produce a dry mixture; ii) softening or melting the mixture; iii) forming the mixture; iv) cooling the mixture; and v) optionally cutting the mixture to a shape, wherein the mixture is formed or cut to a shape having at least one pointed end with an included angle of between about 10-50°. The included angle may be between about 10-40°.

This method is particularly suitable where the mixture includes one or more carbohydrates or polyethers as an excipient. Preferably, the excipient is one or more polyethers.

Preferably the method is carried out at a temperature of between 30° C. and 150° C., more preferably in a range of 40° C. to 100° C. While the choice of temperature is partly dependent on the nature of the active material and any excipients, a lower temperature is desired thereby mitigating any damage to and disintegration of the one or more active material.

With either method, the paste or dry mixture may be formed by extrusion, tabletting or injection moulding. Ideally, the paste or dry mixture is formed by extrusion through a die.

However, extrusion has its difficulties and drawbacks and the design of the die is also important. For small scale formulation work or when working with potent drugs where batch sizes, even at a commercial scale, will be small, the Applicant has found that it is more efficient to use a ram extruder rather than a screw extruder. In particular, it has been found that a screw extruder results in relatively large quantities of material being wasted in the screw. Thus, a ram extruder is preferred to produce a higher yield.

To assist with extrusion, the die itself may be heated so that all of the mixture in the die is in the same physical form before extrusion. Alternatively, the heating elements might be towards the exit of the die, causing the material on the outside of the mixture to melt or soften during the extrusion process without affecting the core of the extrudate.

The extruded lengths of material need to be cut before they can be administered via a drug delivery system. The cutting can be undertaken with a range of different processes including a blade (hot or cold), ultrasound, a laser or a water jet. The paste may therefore be cut using cutting means selected from the group consisting of a blade, ultrasound, a laser, and a water jet. The cutting means may be either hot or cold, for example, the laser is likely to be hot. The cutting means may be heated or at room or ambient temperature.

The paste may be cut, for example by using a blade, while the extrudate is still soft. The paste may be cut, for example by using a heated blade, when the extrudate is dry and solid.

The cutting process used will determine the preferred state for the extrudate. Advantageously the extrudate is cut using a blade. If a sharp cold knife is used then the extrudate is preferably cut while still soft. The blade may be like a guillotine or a rotating blade. If a heated blade is used, the extrudate is advantageously cut while the material is dry and solid, but may also be used to cut the extrudate when in the form of a soft paste. Again, either a guillotine or rotary blade can be used but the hot blade will cause the material along the cut faces to melt or soften as it cuts.

Ultrasonic cutters are typically used with soft materials and lasers may be used with either soft or hard materials.

There are alternative manufacturing techniques to extrusion. The first of these is a standard tabletting process. The main drawback with tabletting is to achieve a consistent fill of material into the tablet press and then to compress the material consistently without damaging the tools. It may also prove difficult to produce a tablet that has a point on one end and if this process is used, the point may have to be cut as a separate process.

If a hot melt process is utilized, an alternative process is to mould the desired material using a standard injection moulding technique. In this case the individual body may be moulded with a pointed end, or a longer body may be moulded and then individual bodies cut to size and shape.

In a yet further embodiment, the method further comprises adding one or more disintegrants or controlled release agents to the active material or dry mixture.

In a still further alternative, the body may have an inert pointed end with the elongate part of the body comprising the active material. Accordingly, the pointed end may be moulded and the subsequent pieces of body comprising the at least one active material might be separately moulded, tabletted, extruded, spray dried or using any other standard manufacturing process.

The formulation of the invention or the body of the invention, when made by either method, is preferably provided with a packaging, such as a cap, cartridge, carousel or cassette. While standard packaging may be used, it is advantageous if the body is packaged with the packaging set out in WO 2004/014468, the full content of which is incorporated herein.

In particular, the packaging comprises a) a housing having a channel running there through and in which is disposed a drive pin or other element, and b) the formulation or body of the present invention. The formulation or body is disposed distal to the drive pin. The housing comprises i) a region allowing the packaged vaccine to be slidably mounted to a suitable delivery device; and ii) an end adapted to engage and tension the skin.

In the following description, the phrase 'packaged vaccine' can be taken to mean 'packaged drug', and vice versa. Preferably the packaged vaccine or drug takes the form of a disposable end cap, cartridge, cassette or carousel, containing a single or multiple doses of the vaccine.

Advantageously, the region for engaging the packaged vaccine or drug to the delivery device in a slidable manner additionally comprises a means for positively locking it to the device such that housing is able to slide within the device but not fall out under gravity. Such a means might be a sprung pin or spigot which exerts a frictional force against the device or a mechanism whereby the packaged vaccine or drug is inserted in a particular orientation and turned so that it is precluded from being removed unless it is turned back into the position in which it was allowed to enter.

In one embodiment, the drive pin or element may have a plurality of flexible or frangible arms extending from its main body. These arms extend outwards (splay) when they ride over a ramped surface provided on the housing, are forced away from the body, and ride over a lip on the housing as a consequence of the flex or frangibility. Where the arms are frangible, the arms will snap off as a result of an area of weakness formed about the shoulder region and fall into a cavity about the ramped region. A frangible system has two advantages: firstly it should ensure full injection occurs, and secondly it will prevent the packaged vaccine or drug from being re-used. The ramp is preferably circular in design, taking the form of a frustoconical surface. This has the advantage that it can be easily moulded and does not require the arms to be orientated for contact.

The packaged vaccine or drug may be sealed in a foil pouch or the like to prevent ingress of, for example, moisture, oxygen, light, bacteria or other vaccine or drug degrading or contaminating agents.

Preferably the end of the packaging adapted to engage and tension the skin comprises one or more projections about the channel exit, most preferably in the form of an annular ring, as such an arrangement most effectively tensions the skin.

A retention system may advantageously be employed to hold the formulation or body of the invention in place in the channel. This might be achieved by, for example, extruding or moulding the body with a number of small splines or other features on its outer surface. These splines or other features should provide a frictional fit without prohibiting the vaccine or drug from being administered. Alternatively, the channel of the packaging might have a small feature, such as a retaining bump or other projection, over which the formulation or body must be pushed.

A tamper or use evident seal or other indicator means may additionally be placed over the top end of the packaged vaccine or drug so it is apparent to the user that the packaged vaccine or drug has not been interfered with and/or is spent.

Additionally or alternatively, a seal may be placed over the exit of the channel of the packaged vaccine or drug. It is preferable to remove this seal prior to administration of the vaccine or drug but, ideally, the seal should be designed such that administration may be carried out through the seal in case the seal is accidentally left on the packaging during administration.

Suitable delivery devices are also described in GB Application No. 0703507.4 and WO 03/023773, as well as WO 2004/014468 and WO 2006/082439, the contents of which are incorporated herein by reference. Suitable solid therapeutic formulations are propelled at low velocity from a needleless device, known as the Glide SDI™ (Solid Dose Injector).

The Glide SDI™ injects the antigen or drug in a solid dosage form through the skin and does not require a needle. The technology comprises a small, single use, disposable cassette that contains the vaccine or drug and a reusable, spring powered actuator.

The Glide SDI™ comprises a small, low cost, disposable cassette carrying the vaccine or drug formulation that is used once and then thrown away. The actuator may be used hundreds of times and is spring powered. The vaccine or drug for the Glide SDI™ may be stored in a solid dosage form and therefore is expected to be more stable than a standard liquid vaccine or drug. This offers the potential for a longer shelf life or even to avoid cold chain storage. The Glide SDI™ is very easy to use and does not require a trained healthcare professional for use. This might be particularly important in the case of a pandemic or a terrorist attack. Needle phobia is not a major issue in developing countries and is not likely to be an issue in the case of a pandemic. Very few people like needles and therefore a needle-free system will help compliance rates in industrialised nations, especially amongst children. The Glide SDI™ makes a pin-point mark on the skin, the same as is left following an injection with a needle and syringe, and so causes no adverse effects. The Glide SDI™ does not require a needle and therefore there are none of the dangers associated with needle-stick injuries, needle reuse and cross-contamination. The Glide SDI™ has a small, light-weight, disposable cassette carrying the vaccine or drug formulation which means the vaccine or drug is easier and lighter to transport than a liquid vaccine or drug in a glass vial and so will be quick to distribute. This is particularly important in the case of emergencies, a terrorist attack or a pandemic outbreak.

In this way, the present invention addresses all of the key features cost, stability, ease of use, needle phobia, adverse effects, cross-contamination and quick distribution. Equally, the present invention provides a solution that is suitable for use in all three areas of the vaccine industry as well as for the injection of drugs in both a home environment or in a healthcare setting.

The Glide SDI™ injects the vaccines and drugs through the skin. Thus, the antigen or drug may be injected into the muscle or subcutaneous tissue. Alternatively, and particularly in, the case of vaccines, some of the antigen may be left in the dermis, making best use of the immunological properties of the skin. This may be achieved by injecting the solid dose parallel with the skin (by taking a pinch in the skin prior to the injection) and/or by leaving the trailing end of the formulation level with the skin surface.

The Glide SDI™ injects vaccines in a solid dosage form making it easy for adjuvants such as alum, gold particles or PLGA particles to be used in the formulations. If the adjuvant particles need to be injected with a needle and syringe, this limits the size of particles to avoid clogging of the needle.

Thus, in a yet further aspect, the invention resides in a drug delivery device comprising a packaged vaccine or drug as set out above. While any suitable drug delivery device may be used, it is preferred that the device is as set out and described in WO 2004/014468, the full contents of which are incorporated herein. The device comprises i) a housing; ii) means for generating a force capable of pushing the formulation from the packaging into a human, animal or avian body; iii) means for transmitting the force to push the formulation from the packaging into the human, animal or avian body; and iv) means for triggering the device.

Such a device may be a reusable device which further comprises means for receiving the packaged vaccine or drug of the invention and means for priming the device.

Alternatively the device may be a single use device in which case the packaged vaccine or drug might be an integral part of the device. Such a device can be provided in a pre-primed form which simply requires triggering, or in a form requiring it to be primed.

In a preferred embodiment, the device may only be actuated by inserting the packaged vaccine or drug and pushing a skin tensioning end of the packaged vaccine or drug against a solid object. The priming and actuation of the device by pushing the end of the device against the skin ensures that there is a reliable and consistent contact and tensioning of the skin on delivery of the vaccine or drug. Additionally, by setting the device so that the force required to actuate it is from, for example, 10-30 Newton, the force will be too high for a patient to actuate the device accidentally without pushing it firmly against the body's tensioned skin, thereby providing a significant safety feature.

The addition of a spring and cap arrangement makes it possible to adjust the actuation force by altering the tension on the spring. By screwing the cap further onto an upper barrel of the device, the spring is tensioned and, by unscrewing it, the force can be reduced. Alternatively, instead of a coil spring as the main power source, the device could incorporate any other type of mechanical spring or a gas spring. In an alternative embodiment the spring could be pre-tensioned during manufacture to avoid having to tension the spring during the vaccine or drug administration. This would result in a single use device in which, as mentioned above, the packaged vaccine or drug would most likely be an integral part of the device.

The velocity of an impact hammer within the device during administration of the formulation is less than 50 m/s, more preferably less than 20 m/s, more preferably still less than 10 m/s. The skilled person will appreciate that the actual speed may vary with the mass of the impact hammer and thus the impact imparted on the formulation. As a consequence the body is delivered by a pushing action from the end of the packaged vaccine or drug rather than by a firing action (as would be the case with a bullet leaving the barrel of a gun).

To ensure that the device actuates automatically when the correct force is applied, the hammer may include a shaped shoulder region which engages a correspondingly shaped surface in a wall separating upper and lower barrels of the device. Such a device will actuate only when the substantially frustoconical sections fully engage. This will be at the same main spring tension every administration and, if the administration is aborted before the frustoconical sections engage, the packaged vaccine or drug can be removed safely without leaving the device primed.

In a preferred embodiment, the device cannot be primed until the packaged vaccine or drug is attached thereto since it is the packaged vaccine or drug that acts against a piston in the device to cause the spring to be tensioned. This makes the device particularly safe. It also means the device cannot be actuated unless and until it is loaded such that an operator is not able to use the device in a belief they are providing an injection.

In the case of a reusable device, a slewing spring may be used to return the impact hammer into its non axially aligned position at the end of each administration.

Furthermore, because the reusable components of the system (all components except those of the packaged vaccine or drug) do not come into contact with the target tissue for administration of the vaccine, they do need to be sterile.

All components, apart from any springs, are preferably moulded making the device cheap to manufacture. The limited number of parts and their ease of assembly keeps manufacturing costs to a minimum.

From another aspect, the present invention encompasses use of the solid dose formulation described above in the preparation of a medicament for the treatment of an infection with a pathogen or a tumour cell.

Alternatively, the present invention encompasses use of the solid dose formulation described above in the preparation of a medicament to enhance an immune response to one or more antigens, or antigenic or immunological agents.

Ideally, the use of the medicament is prophylactic to reduce the likelihood of infection. Alternatively, the use may be curative, post-infection.

In a preferred embodiment, the medicament is for dermal, intradermal, transdermal, subcutaneous or intramuscular administration.

Ideally, the formulation enhances the immunogenicity of the one or more antigens. Alternatively, the dermal, intradermal, transdermal, subcutaneous or intramuscular administration enhances the immunogenicity of the one or more antigens.

From a yet further aspect, the present invention resides in a method of vaccination of a vertebrate, such as mammal or bird, from infection with a pathogen or a tumour cell. The method comprises administering an immunogenically or antigenically effective amount of a solid formulation comprising one or more antigenic or immunogenic agents.

Expressed in another way, the invention resides in a method for eliciting an enhanced immune response from an antigenic or immunogenic agent in a vertebrate, the method comprising dermal, intradermal, transdermal, subcutaneous or intramuscular administration of a solid vaccine composition, wherein the solid vaccine composition comprises an effective amount of one or more antigenic or immunogenic agents.

As described above, an effective amount of antigenic or immunogenic agent could be 75%, 50% or 25% by weight of the dose required for a liquid formulation injected with a needle and syringe. In other words, the effective amount of antigenic or immunogenic agent might be one tenth of one hundredth or even one thousandth of the dose required for a liquid formulation injected with a needle and syringe.

A reduction in the amount of antigenic or immunogenic agent in the solid formulation might also lead to an equivalent reduction in the amount of adjuvant required in the formulation. A solid formulation, in itself, might act as an adjuvant in the skin thus allowing a further reduction in the dose of adjuvant particles that might be added to the solid formulation.

From another angle, the invention relates to a method of enhancing direct or subsequent immunological responses to one or more antigens in a vaccine formulation, the method comprising administering the one or more antigens in a solid formulation.

Alternatively, the present invention is directed to a method for enhancing the immunogenicity of one or more antigens, the method comprising administering an effective amount of the one or more antigens in a solid formulation through the skin, subcutaneous layer or muscle of a vertebrate, such as a mammal or bird.

In a yet further alternative, the method encompasses a method of promoting highly efficient antigen presentation in a vertebrate, such as a mammal or bird, comprising exposing the vertebrate to a solid formulation of the antigen.

Advantageously, the solid composition or formulation is formulated in a formulation as described above.

Ideally, the formulation is administered dermally, intradermally, transdermally, subcutaneously or intramuscularly. The Applicant has found that administration of the formulation in a plane parallel to the surface of the kin is effective.

It is advantageous if administration is by way of a needle-free delivery system. Preferably, the delivery system administers the formulation using a low velocity, pushing force. The velocity may be less than 50 m/s, preferably less than 20 m/s and more preferably less than 10 m/s.

Aspects of the present invention will now be described further by way of non-limiting examples, in which:

Figure 1:
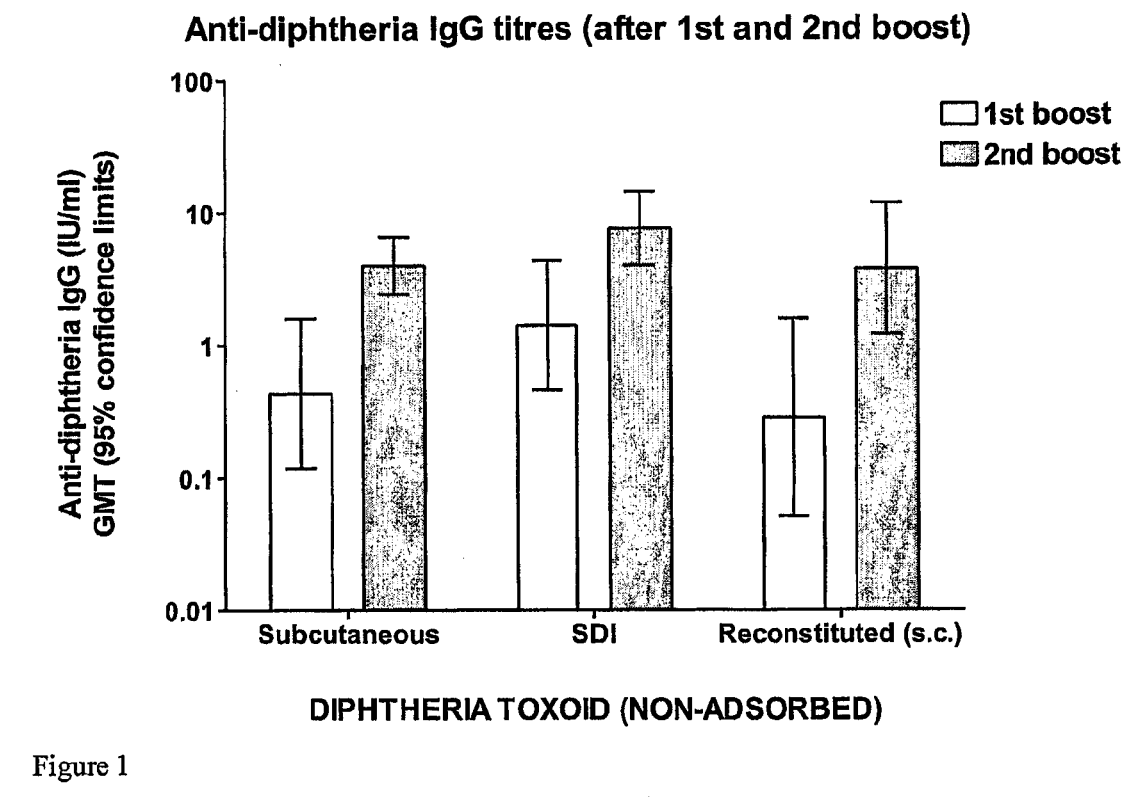

FIG. 1 shows anti-diphtheria IgG titres after first and second boosts of non-adsorbed diphtheria toxoid. Subcutaneous needle and syringe administration, Glide SDI™ administration and subcutaneous administration of reconstituted SDI™ solid formulation were compared. Clear bars represent the first boost; grey bars represent the second boost.

FIG. 2 shows anti-DTx neutralising antibody titres after first and second boosts of non-adsorbed diphtheria toxoid. Subcutaneous needle and syringe administration, Glide SDI™ administration and subcutaneous administration of reconstituted SDI™ solid formulation were compared. The clear boxes represent the first boost while grey boxes represent the second boost.

Figure 3:
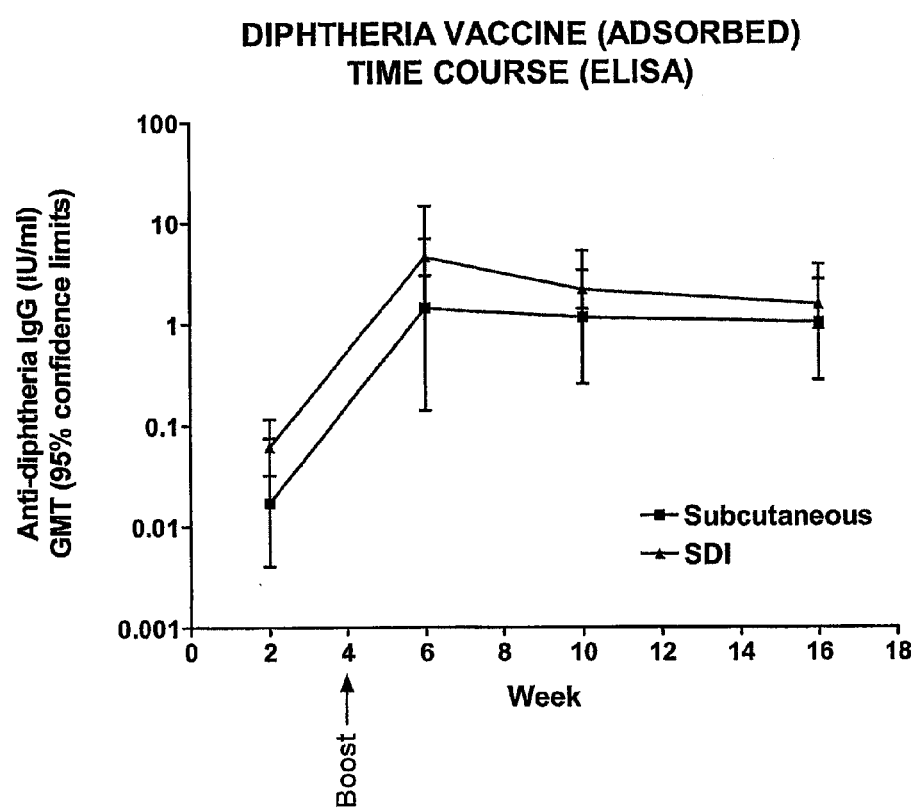

FIG. 3 shows anti-diphtheria antibody titres measured by ELISA over a course of fourteen weeks, with a boost given four weeks after the prime administration of adsorbed diphtheria vaccine. Square symbols represent the needle and syringe subcutaneous administration. The triangle symbols represent administration by Glide SDI™.

Figure 4:
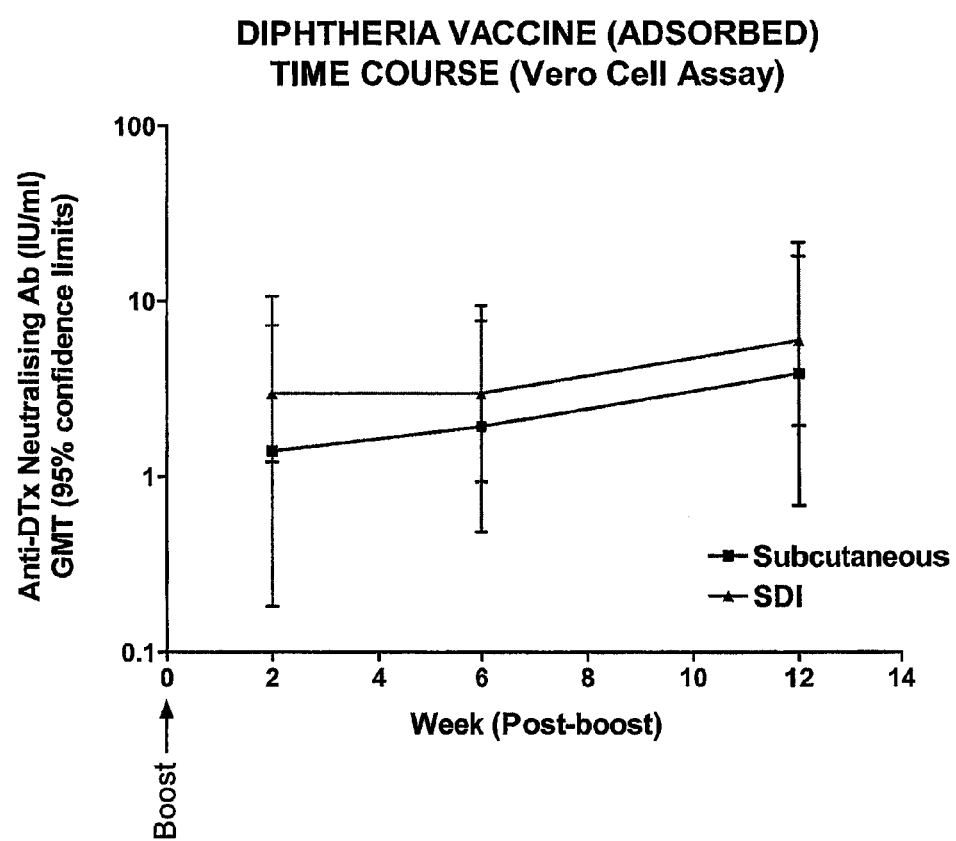

FIG. 4 shows anti-diphtheria toxin neutralizing antibody in IU/ml after administration of adsorbed diphtheria vaccine expressed against a reference guinea pig serum calibrated in IU/ml. Square symbols represent the needle and syringe subcutaneous administration. The triangle symbols represent administration by Glide SDI™.

Figure 5:
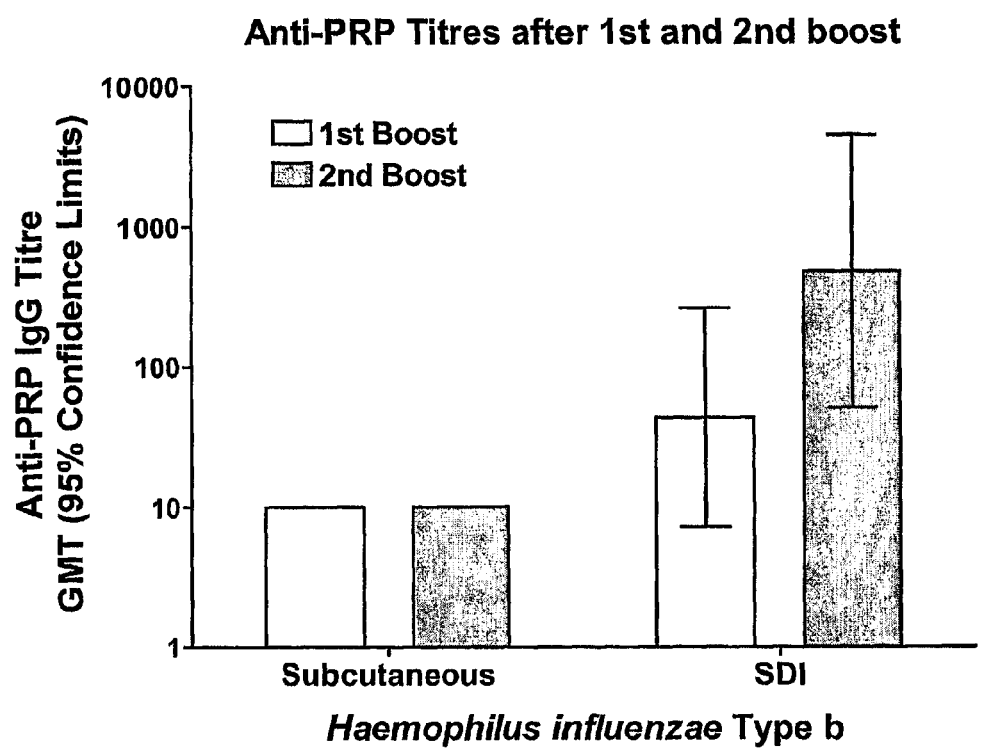

FIG. 5 shows anti-PRP antibody titres two weeks after a first boost (red bars) and two weeks after a second boost (blue bars) of *Haemophilus influenzae* type b (Hib) vaccine administered via needle and syringe or Glide SDI™. The anti-PRP IgG titre is a log scale. A titre of 10 for the subcutaneous arm is the lower limit of detection for the assay and indicates no measurable response.

EXAMPLE 1

The data provided below suggests that the solid formulation of the present invention produces a more consistent and reliable immune response than a standard needle and syringe injection.

A standard diphtheria vaccine without any adjuvant was formulated into material suitable for delivery with the Glide SDI™. A formulation with approximately 2 Lf per dosage was used in a guinea pig model. The excipient used for these solid formulations was sorbitol. The following groups were compared:

1. Standard needle and syringe;
2. Glide SDI™; and
3. Glide SDI™ formulation reconstituted and injected through a needle and syringe.

The animals had a prime injection with boost injections after four and eight weeks. Two weeks after each boost blood samples produced the anti-diphtheria antibody titres shown in FIG. 1. For the Anti-diphtheria IgG ELISA the results are expressed as anti-diphtheria IgG antibodies in International Units per ml (IU/ml) against a reference guinea pig serum calibrated in IU/ml. Limit of detection=0.001 IU/ml Functional toxin-neutralising antibody measurements were made using a vero cell assay. Results are shown in the FIG. 2 where anti-diphtheria toxin neutralizing antibody in IU/ml is expressed against a reference guinea pig serum calibrated in IU/ml. Limit of detection=0.0075 IU/ml.

There is no significant difference in the results seen with the three cohorts above although it is thought that the responses in this animal model are possibly maximised in this study. It can be seen with Example 3 below that when antigen dosing is reduced, a difference in efficacy is seen between standard needle and syringe administration compared to a solid dosage form.

EXAMPLE 2

An adjuvanted diphtheria vaccine was formulated into material suitable for delivery with the Glide SDI™. The adjuvant was aluminium hydroxide (alum) and the excipient was sorbitol. A formulation with approximately 2 IU (approximately 0.9 Lf) per dosage was used in a guinea pig model. The following groups were compared:

1. Standard needle and syringe; and
2. Glide SDI™.

The animals had a prime injection with a single boost injection after four weeks. Blood samples were taken two weeks after the prime injection and at two, six and twelve weeks after the boost injection. The anti-diphtheria antibody titres measured are shown in FIG. 3. These data are measured in the same manner as for Example 1.

Functional toxin-neutralising antibody measurements were made using a vero cell assay, as outlined in Example 1. The results shown in FIG. 4 are expressed as anti-diphtheria toxin neutralizing antibody in against a reference guinea pig serum calibrated in IU/ml.

It can be seen that there is no significant difference between the mean results for the two delivery techniques. However, the variability of response to immunisation is lower in the group immunised with the Glide SDI™. It is of note that the kinetics of the antibody response post-boost differs between total antibody titres and functional neutralising antibody titres. While total antibody levels remain constant or fall slightly in the weeks post boost, functional antibody levels are higher 12 weeks after boost compared to those measured 2 weeks after boost.

EXAMPLE 3

A standard *Haemophilus influenzae* type b (Hib) vaccine (which does not contain an adjuvant) was formulated into material suitable for delivery with the Glide SDI™. A formulation with approximately 1/40 of a standard human dose was used in a guinea pig model. The excipient used was sorbitol. The following groups were compared:

1. Standard needle and syringe; and
2. Glide SDI™.

The animals had a prime injection with boost injections after four and eight weeks. Two weeks after the first boost and two weeks after the second boost blood samples produced the anti-PRP antibody titres shown in FIG. 5.

It can be seen that the Glide SDI™ produced a low but measurable immune response two weeks after the first boost and this was further enhanced with the second boost. The standard needle and syringe injections did not produce an immune response with this does of Hib in guinea pigs. These data indicate a dose sparing effect compared to a standard needle and syringe injection as well as a more consistent and reliable response.

In addition to the measurement of antibody titres a functional protection test was undertaken. Infant rats (3-5 days old) were injected i.p. with 100 μl of pooled immune serum (diluted 1:1 with saline) on day 1. After 24 hours (day 2), the animals were challenged with $1\times10^4$ CFU of Hib (Eagan strain). After another 24 hr (day 3) animals were bled and triplicates of 10 μl of blood were cultured for the presence of Hib bacteria on chocolate agar blood for 24 hours.

The results showed that the immune sera induced by the Glide SDI Hib dosages induced 100% protection in the infant rat bacteraemia model (10/10 animals had no bacteraemia). Sera from subcutaneous needle and syringe Hib cohort induced only 50% protection (5/10 animals had no bacteraemia).

These data demonstrate that the Glide SDI produced protective antibodies compared to the needle and syringe cohort in this study.

EXAMPLE 4

10 grammes of sorbitol powder were mixed with 1.5 ml of water and a smooth dry paste was produced. The paste was added to the barrel of a ram extruder and the mixture was extruded through a die with an exit hole of 0.9 mm diameter. The resultant extrudate was a smooth rod of material which was allowed to dry overnight in a desiccant chamber. The material, when as cut with a warm blade and individual dosages were formed with a flat end on one end and a point on the other end. The pointed end had an included angle of approximately 23 degrees and a length of approximately 4 mm. Short rods of the same material of approximately 6 mm in length were cut with a flat end on both ends. These rods were tested on a force meter for their longitudinal crush strength which was approximately 10N. The dosages having a pointed end were successfully injected into pig skin, ex vivo, using the Glide technology as described in WO 03/023773 and WO 2004/014468 (developed by Glide Pharma, Abingdon, UK.) demonstrating that this placebo formulation could be delivered to human tissue, if desired.

EXAMPLE 5

1.8 grammes of sorbitol powder were weighed out. 200 milligrammes of fentanyl citrate was added to approx 300 microliters of water and allowed to dissolve. The solution was added to the sorbitol powder and produced a smooth dry paste. The paste was processed and tested in the same manner as outlined in Example 1 and no difference was seen in any of the results. The quantity of fentanyl added to the formulation was a typical adult dose per final dosage. A number of the individual dosages were assayed for content of fentanyl and very good homogeneity had been achieved through the mix.

EXAMPLE 6

2 grammes of sumatriptan succinate were mixed with 2 grammes of polyethylene glycol. The mix was heated to approximately 70° C. and extruded as a smooth rod through a die with an exit diameter of approximately 1.0 mm. On cooling, the extrudate solidified and could then be cut into individual lengths and tested as outlined in Example 1. The dosages were successfully delivered to pig skin, ex vivo, using the Glide technology.

EXAMPLE 7

500 mg of sodium alginate was mixed with 500 mg of sumatriptan succinate. 450 microliters of water was added and a smooth material was extruded which, when dried, was approximately 0.77 mm in diameter. Short lengths of this material had a longitudinal crush strength of approximately 42N. Sodium alginate can be used as an excipient in lower concentrations in formulations which still have sufficient strength to penetrate pig skin, ex vivo, using the Glide Technology.

We claim:

1. An elongate body for parenteral injection at low velocity from a device, the body having a compressive strength between 50 and 500 Newton and a pointed end having an included angle of between 10-50°, wherein the body is at least partly crystalline, does not contain a coating, and comprises at least one active material, the at least one active material being a peptide, a protein, a DNA, an RNA, a small molecule, a labelled molecule, a dye, an antigen, a vaccine, a whole cell vaccine, a killed micro-organism, an attenuated micro-organism, an inactive toxic compound, or a polysaccharide.

2. An elongate body for parenteral injection at low velocity from a device, the body having a compressive strength between 50 and 500 Newton and at least one pointed end having an included angle of between 10-50°, wherein the body is at least partly crystalline, does not contain a coating, and comprises at least one active material, the at least one active material being a peptide, a protein, a DNA, an RNA, a small molecule, a labelled molecule, a dye, an antigen, a vaccine, a whole cell vaccine, a killed micro-organism, an attenuated micro-organism, an inactive toxic compound, or a polysaccharide.

3. The body of claim 2, wherein the at least one pointed end has an included angle of between 20-30°.

4. The body of claim 3, wherein the pointed end has an included angle of 23°.

5. The body of claim 2, wherein the pointed end has a tip that is flat, conical, part spheroidal, sphenoidal, or fractured.

6. The body of claim 1, wherein the at least one active material is a pharmaceutically active material.

7. The body of claim 1, wherein the active material is present in an amount of between 0.1% and 99.9% by weight.

8. The solid vaccine formulation comprising the body of claim 1, the formulation being parenterally administerable without a needle, the formulation comprising at least one antigenic or immunogenic agent, and optionally at least one excipient.

9. The vaccine formulation of claim 8, wherein the at least one antigenic or immunogenic agent is adsorbed onto the surface of the body.

10. The vaccine formulation of claim 8, wherein the at least one antigenic or immunogenic agent is dispersed homogeneously throughout the body.

11. The vaccine formulation of claim 8, wherein the body has an inert pointed end, and the at least one antigenic or immunogenic agent is dispersed in the elongate part of the body.

12. The vaccine formulation of claim 8, wherein the body has an inert pointed end, and the at least one antigenic or immunogenic agent is adsorbed on the elongate part of the body.

13. The vaccine formulation of claim 8, further comprising at least one adjuvant.

14. The vaccine formulation of claim 13, wherein the at least one adjuvant is aluminium hydroxide.

15. The vaccine formulation of claim 8, wherein the formulation comprises more than one dose of the antigenic or immunogenic agent.

16. The vaccine formulation of claim 15, wherein the formulation comprises a prime and at least one boost dose of the antigen.

17. The vaccine formulation of claim 16, wherein the formulation comprises more than one boost dose of the antigenic or immunogenic agent.

18. The vaccine formulation of claim 8, wherein the formulation comprises more than one formulation of the antigenic or immunogenic agent.

19. The body of claim 1 wherein the active material includes or is included within at least one of an immediate release formulation, a controlled release formulation, a continuous release formulation and a pulsed release formulation.

20. The vaccine formulation of claim 8, wherein the antigenic or immunogenic agent content of the formulation is between 0.01% and 100% by weight.

21. The vaccine formulation of claim 8, wherein the at least one antigenic or immunogenic agent is diphtheria toxin, a *Haemophilus influenzae* type b (Hib) antigen or immunogen, or a tumor specific antigen.

22. The vaccine formulation of claim 8, wherein the excipient is a bulking agent, an anti-oxidant, a disintegrant, a binder, a biodegradable polymer, a salt, a buffer, a wetting agent, an adjuvant, a stabilising agent, a binder, a filler, a chemical stabilizer, a sugar, a polyether.

23. The vaccine formulation of claim 8 in the form of a dermal, intradermal, transdermal, subcutaneous or intramuscular administerable formulation.

24. The body of claim 1, wherein the active material is homogeneously dispersed throughout the body.

25. The body of claim 2, wherein the at least one pointed end of the body contains a non-active material.

26. The body of claim 25, wherein the active material is separated from the non-active material in the body.

27. The body of claim 1, wherein the body has a cross-sectional shape that is ovoid, triangular, circular, round, rectangular or polygonal.

28. A package comprising the vaccine formulation of claim 8.

29. The body of claim 1, wherein the active material is present in an amount of between 0.1 and 60% by weight.

30. The body of claim 1, wherein the active material is present in an amount of between 0.1 and 35% by weight.

31. The vaccine formulation of claim 8, wherein the antigenic or immunogenic agent content of the formulation is between 0.01% and 60% by weight.

32. The vaccine formulation of claim 8, wherein the antigenic or immunogenic agent content of the formulation is between 0.01% to 35% by weight.

33. The vaccine formulation of claim 8, wherein the antigenic or immunogenic agent content of the formulation is between 0.5% and 99.9% by weight.

34. The vaccine formulation of claim 8, wherein the antigenic or immunogenic agent content of the formulation is between 0.5% and 60% by weight.

35. The vaccine formulation of claim 8, wherein the antigenic or immunogenic agent content of the formulation is between 0.5% and 35% by weight.

* * * * *